US012571041B1

(12) United States Patent
Wadsworth et al.

(10) Patent No.: US 12,571,041 B1
(45) Date of Patent: Mar. 10, 2026

(54) FRAGMENTING RNA:DNA HYBRIDS

(71) Applicant: Watchmaker Genomics, Inc., Boulder, CO (US)

(72) Inventors: Ross Wadsworth, Cape Town (ZA); Lee French, Cape Town (ZA); Bryce Foster, Cape Town (ZA); Lianna Kapp, Cape Town (ZA)

(73) Assignee: Watchmaker Genomics, Inc., Boulder, CO (US)

( * ) Notice: Subject to any disclaimer, the term of this patent is extended or adjusted under 35 U.S.C. 154(b) by 0 days.

(21) Appl. No.: 19/375,973

(22) Filed: Oct. 31, 2025

Related U.S. Application Data

(60) Provisional application No. 63/736,649, filed on Dec. 20, 2024.

(51) Int. Cl.
*C12Q 1/6874* (2018.01)
*C12Q 1/6806* (2018.01)

(52) U.S. Cl.
CPC ......... *C12Q 1/6874* (2013.01); *C12Q 1/6806* (2013.01)

(58) Field of Classification Search
CPC ............................ C12Q 1/6874; C12Q 1/6806
See application file for complete search history.

(56) References Cited

FOREIGN PATENT DOCUMENTS

EP 3235905 A1 * 10/2017 ......... C12N 15/1093

OTHER PUBLICATIONS

Vvedenskaya et al., "Preparation of cDNA libraries for high-throughput RNA sequencing analysis of RNA 5' ends", PMC, January, pp. 1-18. (Year: 2016).*

* cited by examiner

*Primary Examiner* — Young J Kim
(74) *Attorney, Agent, or Firm* — Wolf, Greenfield & Sacks, P.C.

(57) ABSTRACT

This disclosure provides methods of fragmenting RNA: DNA hybrids. These methods can be used to improve preparation of RNA for next-generation sequencing.

18 Claims, 9 Drawing Sheets

Specification includes a Sequence Listing.

SEQUENCE LISTING

```
Sequence total quantity: 3
SEQ ID NO: 1            moltype = AA  length = 155
FEATURE                 Location/Qualifiers
source                  1..155
                        mol_type = protein
                        organism = synthetic construct
SEQUENCE: 1
MLKQVEIFTD GSCLGNPGPG GYGAILRYRG REKTFSAGYT RTTNNRMELM AAIVALEALK  60
EHCEVILSTD SQYVRQGITQ WIHNWKKRGW KTADKKPVKN VDLWQRLDAA LGQHQIKWEW  120
VKGHAGHPEN ERCDELARAA AMNPTLEDTG YQVEV                             155

SEQ ID NO: 2            moltype = AA  length = 270
FEATURE                 Location/Qualifiers
source                  1..270
                        mol_type = protein
                        organism = synthetic construct
SEQUENCE: 2
WGALGHATVA YVAQHYVSPE AASWAQGILG SSSSSYLASI ASWADEYRLT SAGKWSASLH  60
FIDAEDNPPT NCNVDYERDC GSSGCSISAI ANYTQRVSDS SLSSENHAEA LRFLVHFIGD  120
MTQPLHDEAY AVGGNKINVT FDGYHDNLHS DWDTYMPQKL IGGHALSDAE SWAKTLVQNI  180
ESGNYTAQAI GWIKGDNISE PITTATRWAS DANALVCTVV MPHGAAALQT GDLYPTYYDS  240
VIDTIELQIA KGGYRLANWI NEIHGSEIAK                                   270

SEQ ID NO: 3            moltype = AA  length = 287
FEATURE                 Location/Qualifiers
source                  1..287
                        mol_type = protein
                        organism = synthetic construct
SEQUENCE: 3
MPRLLPISAA TLALAQLTYG WGNLGHETVA YIAQSFVASS TESFCQNILG DDSTSYLANV  60
ATWADTYKYT DAGEFSKPYH FIDAQDNPPQ SCGVDYDRDC GSAGCSISAI QNYTNILLES  120
PNGSEALNAL KFVVHIIGDI HQPLHDENLE AGGNGIDVTY DGETTNLHHI WDTNMPEEAA  180
GGYSLSVAKT YADLLTERIK TGTYSSKKDS WTDGIDIKDP VSTSMIWAAD ANTYVCSTVL  240
DDGLAYINST DLSGEYYDKS QPVFEELIAK AGYRLAAWLD LIASQPS                287
```

FRAGMENTING RNA:DNA HYBRIDS

RELATED APPLICATIONS

This application claims the benefit under 35 U.S.C. § 119 (e) of U.S. Provisional Application No. 63/736,649, filed Dec. 20, 2024, the entire contents of which are incorporated herein by reference.

REFERENCE TO AN ELECTRONIC SEQUENCE LISTING

The contents of the electronic sequence listing (W109470034US01-SEQ-ACZ.xml; Size: 4,329 bytes; and Date of Creation: Oct. 30, 2025) is herein incorporated by reference in their entirety.

BACKGROUND

RNA-sequencing (RNA-seq) has become an important tool in molecular biology, affording high-throughput transcriptome profiling and facilitating differential gene expression analysis, single nucleotide polymorphism identification, and transcript isoform detection. An important step of preparing a high-quality library for RNA-sequencing is the generation of fragments that have a size distribution centered around an average length that is suitable for the type of instrument used for RNA-sequencing.

SUMMARY

RNA-sequencing library preparation protocols typically require RNA extraction, cDNA synthesis of the extracted RNA (which comprises a 1$^{st}$ strand synthesis to obtain a RNA:DNA hybrid, followed by a 2$^{nd}$ strand synthesis to obtain full-length double-stranded cDNA), and adapter ligation prior to sequencing. To generate a high-quality library, fragments that have a size distribution centered around an average length suitable for RNA sequencing are frequently generated during the workflow. Currently, this occurs either by fragmenting the RNA after extraction and prior to cDNA synthesis or by fragmenting the cDNA prior to adapter ligation. However, there are numerous disadvantages to both methods: fragmenting RNA after extraction can flood the library with unwanted RNA fragments and the harsh conditions used for fragmenting RNA can result in degradation and material loss, while fragmenting cDNA prior to adapter ligation can result in fragmentation bias, loss of strand specificity, and requires additional processing steps which can result in material loss.

The inventors of the present disclosure found that these disadvantages can be circumvented by fragmenting the product of the 1$^{st}$ strand synthesis (i.e., a RNA:DNA hybrid), followed by 2$^{nd}$ strand synthesis to yield size-appropriate double-stranded cDNA fragments ready for adapter ligation and sequencing. Surprisingly, the methods of fragmenting RNA:DNA hybrids of the present disclosure were shown to facilitate rapid stranded library preparation for RNA-sequencing applications and significantly reduce workflow time.

Accordingly, in some aspects, this disclosure provides a method of fragmenting an RNA:DNA hybrid, the method comprising: (i) cleaving the RNA of the RNA:DNA hybrid using a ribonuclease to produce single stranded regions of the DNA; and (ii) cleaving the single stranded regions of the DNA using a single-strand-specific nuclease to produce RNA:DNA hybrid fragments. In some aspects, this disclosure provides a method for preparing RNA for sequencing, the method comprising: (i) converting the RNA into an RNA:cDNA hybrid; (ii) fragmenting the RNA:cDNA hybrid into RNA:cDNA hybrid fragments using a ribonuclease and a single-strand-specific nuclease; and (iii) converting the RNA:cDNA hybrid fragments into double-stranded DNA.

In some embodiments, the fragmenting comprises: (a) cleaving the RNA of the RNA:cDNA hybrid using the ribonuclease to produce single-strand regions of the cDNA; and (b) cleaving the single-stranded regions of the cDNA using the single-strand-specific nuclease to produce RNA:cDNA hybrid fragments.

In some embodiments, the ribonuclease is a non-sequence-specific ribonuclease. In some embodiments, the non-sequence-specific ribonuclease is an RNase. In some embodiments, the RNase is RNaseH.

In some embodiments, the single-strand specific nuclease is nuclease P1 or nuclease S1.

In some embodiments, the RNA:cDNA hybrid fragments are 100-1500 base pairs in length. In some embodiments, the RNA:cDNA hybrid fragments are 200-300 base pairs in length.

In some embodiments, converting the RNA into an RNA:cDNA hybrid comprises converting using a reverse transcriptase and primers. In some embodiments, the primers are poly-T primers. In some embodiments, the primers are random primers. In some embodiments, the primers are target specific primers.

In some embodiments, converting the RNA:cDNA hybrid fragments into double stranded DNA comprises using a polymerase. In some embodiments, the polymerase is an *E. coli* Pol I.

In some embodiments, methods of the present disclosure further comprise combining RNA:cDNA hybrid, the ribonuclease, the single-strand-specific nuclease, and polymerase into a single reaction mixture.

In some embodiments, (ii) fragmenting the RNA:cDNA hybrid into RNA:cDNA hybrid fragments using a ribonuclease and a single-strand-specific nuclease; and (iii) converting the RNA:cDNA hybrid fragments into double-stranded DNA occur contemporaneously.

In some embodiments, methods of the present disclosure further comprise A-tailing the double stranded DNA. In some embodiments, methods of the present disclosure further comprise ligating sequencing adaptors onto the double stranded DNA.

In some aspects, this disclosure provides a reaction mixture, comprising: an RNA:DNA hybrid; a ribonuclease; and a single-strand-specific nuclease. In some embodiments, the ribonuclease is RNaseH. In some embodiments, the single-strand-specific nuclease is nuclease P1 or nuclease S1. In some embodiments, the reaction mixture further comprises one or more of a polymerase, zinc ion, and magnesium. In some embodiments, the reaction mixtures further comprises a polymerase, wherein the polymerase is *E. coli* Pol I.

In some aspects, this disclosure provides a kit comprising: a ribonuclease; and a single-strand-specific nuclease. In some embodiments, kits of the present disclosure further comprise reagents for first strand synthesis; and reagents for second strand synthesis. In some embodiments, kits of the present disclosure further comprise one or more of zinc ion, a zinc ion chelator, and magnesium. In some embodiments, kits of the present disclosure further comprise reagents for poly-A tailing of DNA; and/or adaptors and reagents for ligating the adaptors to DNA. In some embodiments, the ribonuclease is RNaseH. In some embodiments, the single-strand-specific nuclease is nuclease P1 or nuclease S1.

In some aspects, this disclosure provides a method of preparing RNA for sequencing, the method comprising: (i) obtaining a plurality of RNAs; (ii) converting RNAs of the plurality of RNAs into RNA:cDNA hybrids using a reverse transcriptase and a plurality of primers that are complementary to the RNAs of the plurality of RNAs; (iii) fragmenting the RNA:cDNA hybrids into RNA:cDNA hybrid fragments, the fragmenting comprising: (a) cleaving the RNA of the RNA:cDNA hybrid using an RNaseH to produce corresponding single strand regions of the cDNA; and (b) cleaving the corresponding single stranded regions of the cDNA using a nuclease P1 to produce RNA:cDNA hybrid fragments; (iv) converting the RNA:cDNA hybrid fragments into double stranded DNAs (dsDNAs) using a polymerase; (v) A-tailing the dsDNAs to produce A tailed dsDNAs; and (vi) ligating sequencing adaptor onto the dsDNAs.

BRIEF DESCRIPTION OF THE DRAWINGS

FIG. 1A shows an exemplary schematic where RNA is fragmented directly before cDNA synthesis and after mRNA capture. FIG. 1B shows an exemplary alternative strategy, in which full-length RNA is reverse transcribed to form full-length double-stranded cDNA molecules prior to enzymatic fragmentation. FIG. 1C shows a schematic of an exemplary strategy provided herein that facilitates the enzymatic fragmentation of RNA:DNA hybrids formed after 1st strand synthesis (SS), followed by 2nd strand synthesis to form blunt-end double-stranded DNA fragments. Modifications to the standard workflow are shown in the shaded box.

DETAILED DESCRIPTION

Figures 1A, 1B, 1C:
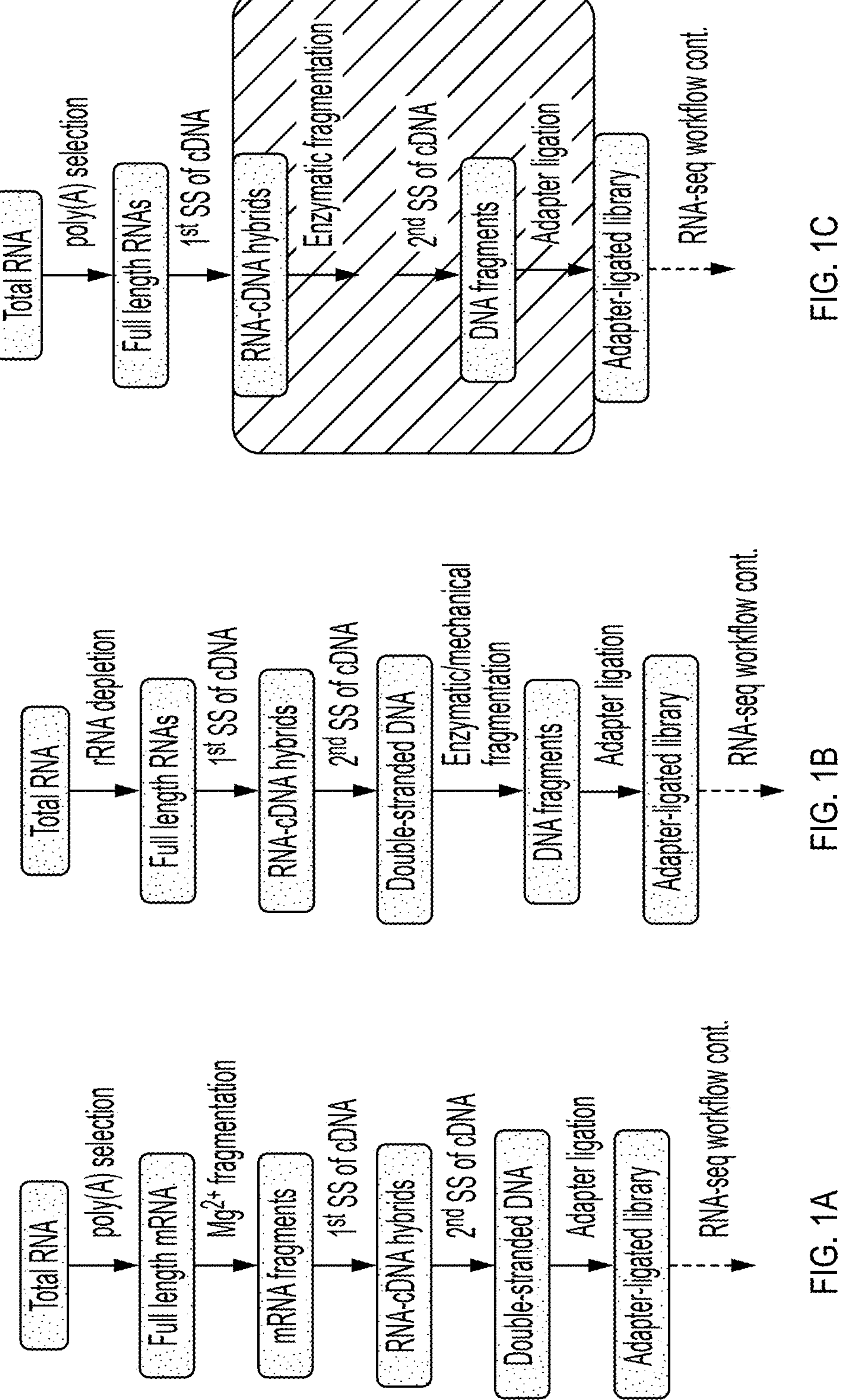
FIGS. 1A-1C show steps of typical RNA-seq library preparation workflows.
Figure 2:
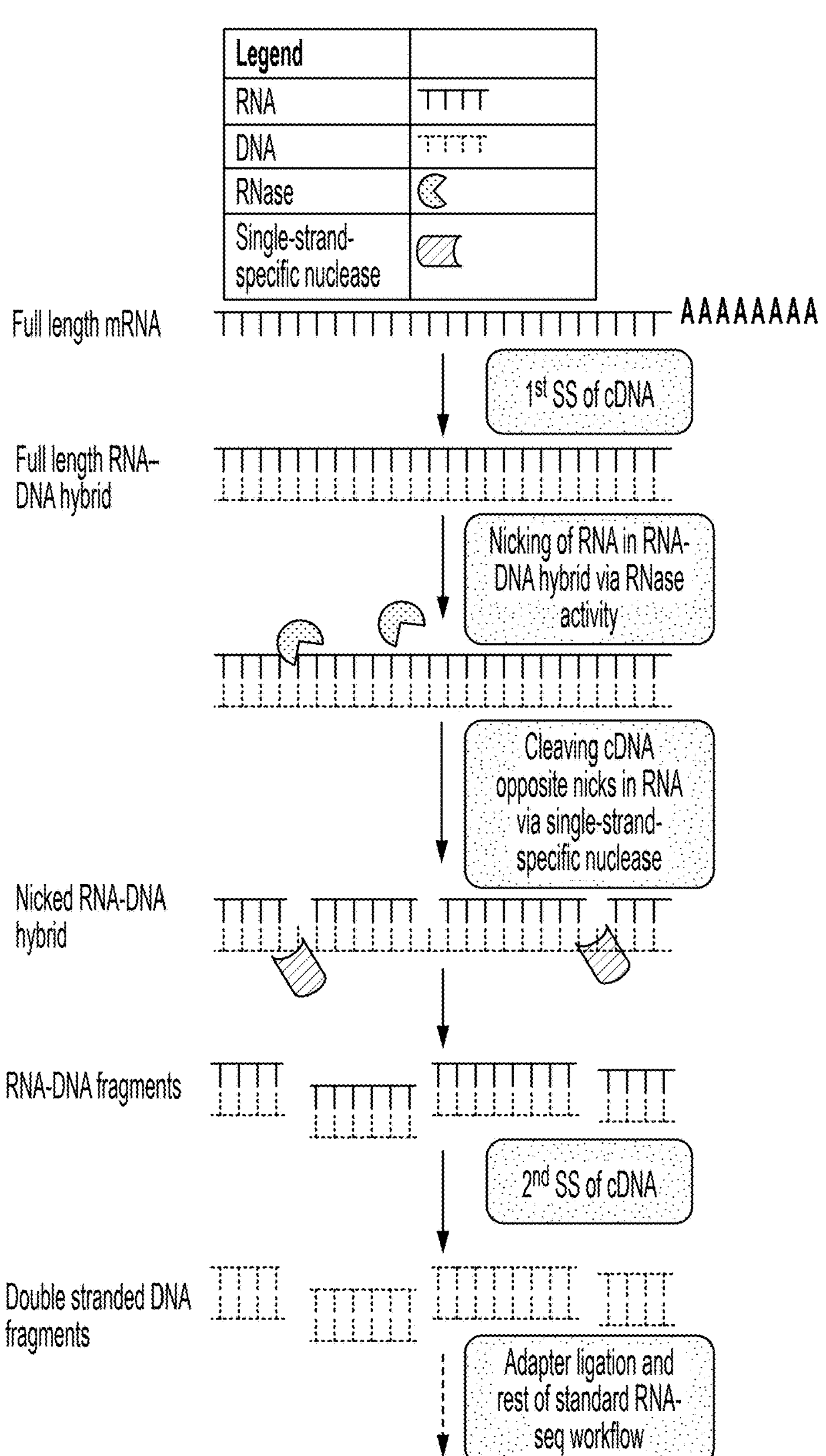
FIG. 2 is a schematic representation of RNA:DNA fragmentation from a non-sequence-specific RNase in combination with a single-strand-specific nuclease. The resulting blunt-end RNA:DNA fragments can be converted to double-stranded DNA fragments that are ready for adapter ligation and sequencing on a high-throughput platform.

Current methods of RNA-sequencing library preparation require a fragmentation step either following RNA extraction and prior to cDNA synthesis, or after cDNA synthesis and prior to adapter ligation. There are numerous drawbacks to both methods: fragmentation of RNA can result in degradation and material loss, while fragmentation of cDNA can result in a loss of strand specificity and requires additional processing steps. However, fragment generation is often needed to obtain a fragment size distribution that is compatible with a chosen sequencing platform.

The inventors of the present disclosure developed methods of fragmenting RNA:DNA hybrids, which allows the generation of an appropriate fragment size distribution while maintaining strand specificity and minimizing material loss. The methods of fragmenting RNA:DNA hybrids of the present disclosure were shown to facilitate rapid stranded library preparation for RNA-sequencing applications and significantly reduce workflow time, while maintaining high data quality suitable for downstream analyses.

Accordingly, in some aspects, this disclosure provides methods of fragmenting RNA:DNA hybrids.

An RNA:DNA hybrid comprises a polynucleotide of deoxyribonucleic acids (i.e., a DNA) that is hybridized to a polynucleotide of ribonucleic acids (i.e., an RNA). In some embodiments, the RNA is a functional RNA (e.g., a ribosomal RNA, a long-noncoding RNA, a miRNA, or a miRNA). In some embodiments, the RNA is a messenger RNA (mRNA). In some embodiments, the RNA is synthetic RNA. In some embodiments, the DNA and the RNA of the DNA: RNA hybrid form a double helix structure (e.g., an A-B double helix). In some embodiments, the DNA is a cDNA. In some embodiments, the DNA is genomic DNA.

"Fragmenting" an RNA:DNA hybrid includes cleaving the RNA and the DNA of the RNA:DNA hybrid to produce two or more RNA:DNA hybrid fragments. In some embodiments, fragmenting the RNA:DNA hybrid comprises producing two or more RNA:DNA hybrid fragments that comprise blunt ends or nearly blunt ends (e.g., overhangs of less than 5 nucleotides, less than 3 nucleotides, or less than 2 nucleotides). In some embodiments, fragmenting the RNA: DNA hybrid comprises cleaving one or more phosphodiester bonds of the RNA and one or more phosphodiester bonds of the DNA.

In some embodiments, cleaving the RNA of the RNA/DNA hybrid comprises cleaving using a ribonuclease. In some embodiments, the ribonuclease is a non-sequence specific ribonuclease. In some embodiments, the ribonuclease is a ribo-endonuclease. In some embodiments, the ribonuclease is a sequence specific ribonuclease. In some embodiments, the ribonuclease is an RNase. In some embodiments, the RNase is *E. coli* RNase H, Tth RNaseH (Thermostable RNase H), RNase If, or RNase A. In some embodiments, the ribonuclease is an RNaseH (e.g., *E. coli* RNaseH). In some embodiments, the ribonuclease is an *E. coli* RNase H. In some embodiments, the *E. coli* RNase H comprises the amino acid sequence of MLKQVE-IFTDGSCLGNPGPGGYGAILRYRGREKTFSAGYTRT-TNNRMELMAAIVALEAL KEHCEVILSTDSQYVR-QGITQWIHNWKKRGWKTADKKPVKNVDLWQR-LDAALGQHQI KWEWVKGHAGHPENERCDELARA-AAMNPTLEDTGYQVEV (SEQ ID NO: 1). In some embodiments, the RNase H comprises an amino acid sequence having at least 95% identity to SEQ ID NO: 1. In some embodiments, the RNase H comprises an amino acid sequence having at least 95% identity to SEQ ID NO: 1 and is catalytically active. In some embodiments, the ribonuclease is a nickase. In some embodiments, cleaving the RNA comprises nicking the RNA. In some embodiments, cleaving the RNA comprises excising one or more nucleotides from the RNA. In some embodiments, cleaving the RNA comprises producing a single stranded region of the DNA of the RNA:DNA hybrid. In some embodiments, cleaving the RNA comprises producing single stranded regions of the DNA of the RNA:DNA hybrid. In some embodiments, a single stranded region of the DNA comprises one nucleotide that is not forming a base pair with the RNA. In some embodiments, a single stranded region of the DNA comprises a nucleotide that is not forming a base pair with the RNA. In some embodiments, a single stranded region of the DNA comprises at least one (e.g., 1, 2, 3, 4, 5, 6, 7, 8, 9, 10, or more) nucleotide(s) that is (are) not forming a base pair with the RNA. In some embodiments, a single stranded region of the DNA comprises at least two nucleotides (e.g., 2, 3, 4, 5, 6, 7, 8, 9, 10, or more) that are not forming a base pair with the RNA. In some embodiments, cleaving the RNA comprises nicking the RNA. In some embodiments, nicking the RNA (e.g., using RNaseH) produces single stranded regions of the DNA. In some embodiments, nicking the RNA (e.g., using RNaseH) produces single stranded regions of the DNA comprises at least one (e.g., 1, 2, 3, 4, 5, 6, 7, 8, 9, 10, or more) nucleotide(s) that does not form a base pair with the RNA. In some embodiments, cleaving the RNA comprises excising one or more nucleotides from the RNA.

In some embodiments, cleaving a single stranded region of the DNA of the RNA:DNA hybrid to produce RNA:DNA hybrid fragments comprises cleaving using a single-strand-specific nuclease. A "single-strand-specific nuclease" refers to a nuclease that preferentially cleaves single stranded polynucleotides over double stranded polynucleotides. In some embodiments, a single-strand-specific nuclease has greater activity and/or binding affinity for singled stranded polynucleotides over double stranded polynucleotides. In some embodiments, a single-strand-specific nuclease is a single-strand-specific DNA nuclease. In some embodiments, the single-strand-specific nuclease is a nuclease P1 or a variant thereof. In some embodiments, the nuclease P1 comprises the amino acid sequence of WGALGHATVAY-VAQHYVSPEAASWAQGILGSSSSSYLASIASWADEY-RLTSAGKWSASL HFIDAEDNPPTNCNVDYERDCGS SGCSISAIANYTQRVSDSSLSSENHAEALRFLVHFIGD MTQPLHDEAYAVGGNKINVTFDGYHDNLHSDWD-TYMPQKLIGGHALSDAESWAKTLV QNIESGNYTAQ-AIGWIKGDNISEPITTATRWASDANALVCTVVMPH GAAALQTGDLYPTY YDSVIDTIELQIAKGGYRLA NWINEIHGSEIAK (SEQ ID NO: 2). In some embodiments, the nuclease P1 comprises an amino acid sequence having at least 95% identity to SEQ ID NO: 2. In some embodiments, the nuclease P1 comprises an amino acid sequence having at least 95% identity to SEQ ID NO: 2 and is catalytically active. In some embodiments, the single-strand-specific nuclease is a nuclease S1 or a variant thereof. In some embodiments, the nuclease S1 comprises the amino acid sequence of MPRLLPISAATLALAQLTYGW GNLGHETVAYIAQSFVASSTESFCQNILGDDSTSY-LANVA TWADTYKYTDAGEFSKPYHFIDAQDNPPQSC GVDYDRDCGSAGCSISAIQNYTNILLESP NGSEAL-NALKFVVHIIGDIHQPLHDENLEAGGNGIDVTY-DGETTNLHHIWDTNMPEEAA GGYSLSVAKTYADLL-TERIKTGTYSSKKDSWTDGIDIKDPVSTSMIWAADAN-TYVCSTVL DDGLAYINSTDLSGEYYDKSQPVFEEL IAKAGYRLAAWLDLIASQPS (SEQ ID NO: 3). In some embodiments, the nuclease S1 comprises an amino acid sequence having at least 95% identity to SEQ ID NO: 3. In some embodiments, the nuclease S1 comprises an amino acid sequence having at least 95% identity to SEQ ID NO: 3 and is catalytically active. In some embodiments, the single-strand-specific nuclease is nuclease P1, nuclease S1, Red, ExoVII, Mung Bean Nuclease or Micrococcal Nuclease. In some embodiments, the method further comprises using a polynucleotide kinase and/or a nicking agent. In some embodiments, the single-strand-specific nuclease is a DNA endonuclease.

In some embodiments, fragmenting the DNA: RNA hybrid comprises producing a plurality of RNA:DNA hybrid fragments. In some embodiments, the majority of RNA: DNA hybrid fragments of the plurality of RNA:DNA hybrid fragments are 100-15,000 nucleotides in length. In some embodiments, the majority of RNA:DNA hybrid fragments of the plurality of RNA:DNA hybrid fragments are 100-10,000 nucleotides in length. In some embodiments, the majority of RNA:DNA hybrid fragments of the plurality of RNA:DNA hybrid fragments are 100-5,000 nucleotides in length. In some embodiments, the majority of RNA:DNA hybrid fragments of the plurality of RNA:DNA hybrid fragments are 100-2500 nucleotides in length. In some embodiments, the majority of RNA:DNA hybrid fragments of the plurality of RNA:DNA hybrid fragments are 100-1,000 nucleotides in length. In some embodiments, the majority of RNA:DNA hybrid fragments of the plurality of RNA:DNA hybrid fragments are 100-500 nucleotides in length. In some embodiments, the majority of RNA:DNA hybrid fragments of the plurality of RNA:DNA hybrid fragments are 200-500 nucleotides in length. In some embodiments, the majority of RNA:DNA hybrid fragments of the plurality of RNA:DNA hybrid fragments are 200-400 nucleotides in length. In some embodiments, the majority of RNA:DNA hybrid fragments of the plurality of RNA:DNA hybrid fragments are 200-300 nucleotides in length.

In some embodiments, the method of fragmenting an RNA:DNA hybrid is performed in conditions suitable for ribonuclease and single-strand-specific nuclease activity (e.g., sufficient for ribonuclease cleavage of the RNA and single-strand-specific nuclease cleavage of the DNA). In some embodiments, the method of fragmenting an RNA: DNA hybrid comprises incubating the RNA;DNA hybrid with a ribonuclease (e.g., RNaseH) at 22-62° C. (e.g., 22-62° C., 32-62° C., 32-52° C., 37-47° C., or 40-44° C.). In some embodiments, the method of fragmenting an RNA:DNA hybrid comprises incubating the RNA;DNA hybrid with a single-strand-specific nuclease (e.g., nuclease P1 or nuclease S1) at 22-62° C. (e.g., 22-62° C., 32-62° C., 32-52° C., 37-47° C., or 40-44° C.). In some embodiments, the method of fragmenting an RNA:DNA hybrid comprises incubating the RNA;DNA hybrid with a ribonuclease (e.g., RNaseH) and a single-strand-specific nuclease (e.g., nuclease P1 or nuclease S1) at 22-62° C. (e.g., 22-62° C., 32-62° C., 32-52° C. 37-47° C., or 40-44° C.). In some embodiments, incubating comprises incubating for less than one hour (e.g., less than 30 minutes, less than 10 minutes, or less than 5 minutes). In some embodiments, incubating comprises incubating for between 5-30 minutes (e.g., between 5-20 minutes, between 5-15 minutes, between 5-10 minutes, between 10-20 minutes, between 10-15 minutes, or between 15-20 minutes).

In some embodiments, this disclosure provides a method of preparing RNA for sequencing. In some embodiments, the method comprises obtaining a plurality of RNAs. In some embodiments, the majority of the RNA in a plurality of RNAs are 20-20,000 nucleotides (e.g., 20-15,000 nucleotides, 20-10,000 nucleotides, 20-7,500 nucleotides, 20-5,000 nucleotides, 20-2,500 nucleotides, 20-1,000 nucleotides, 20-750 nucleotides, 20-500 nucleotides, 20-250 nucleotides, 250-20,000 nucleotides, 250-15,000 nucleotides, 250-10,000 nucleotides, 250-7,500 nucleotides, 250-5,000 nucleotides, 250-2,500 nucleotides, 250-1,000 nucleotides, 250-750 nucleotides, 250-500 nucleotides, 500-20,000 nucleotides, 500-15,000 nucleotides, 500-10,000 nucleotides, 500-7,500 nucleotides, 500-5,000 nucleotides, 500-2,500 nucleotides, 500-1,000 nucleotides, 500-750 nucleotides, 750-20,000 nucleotides, 750-15,000 nucleotides, 750-10,000 nucleotides, 750-7,500 nucleotides, 750-5,000 nucleotides, 750-2,500 nucleotides, 75-1,000 nucleotides, 1,000-20,000 nucleotides, 1,000-15,000 nucleotides, 1,000-10,000 nucleotides, 1,000-7,500 nucleotides, 1,000-5,000 nucleotides, 1,000-2,500 nucleotides, 2,500-20,000 nucleotides, 2,500-15,000 nucleotides, 2,500-10,000 nucleotides, 2,500-7,500 nucleotides, 2,500-5,000 nucleotides, 5,000 nucleotides-20,000 nucleotides, 5,000-15,000 nucleotides, 5,000-10,000 nucleotides, 5,000-7,500 nucleotides, 7,500-20,000 nucleotides, 7,500-15,000 nucleotides, 7,500-10,000 nucleotides, 10,000-20,000 nucleotides, 10,000-15,000 nucleotides, or 15,000-20,000 nucleotides) in length. In some embodiments, a plurality of RNAs comprises at least $10^3$, at least $10^4$, at least $10^5$, at least $10^6$, at least $10^7$, at least $10^8$, at least $10^9$, or at least $10^{10}$ RNAs. The plurality of RNAs may be obtained from any appropriate source including, but not limited to biological samples (e.g., tissue samples, blood samples, plasma samples, serum samples, cerebrospinal fluid samples, saliva samples, or urine samples), cells (e.g., mammalian cells, bacterial cells, yeast cells, insect cells, or plant cells), environmental samples (e.g., soil samples or water samples), or synthetic sources (e.g., chemically synthesized RNAs).

In some embodiments, the method comprises converting the RNA into an RNA:cDNA hybrid (e.g., first strand synthesis). In some embodiments, the method comprises converting RNAs of the plurality of RNAs into RNA:cDNA hybrids (e.g., first strand synthesis). Converting the RNA into an RNA:cDNA hybrid may be performed in any suitable way. In some embodiments, converting the RNA into an RNA:cDNA hybrid comprises hybridizing the RNA with a primer that is complementary to the RNA, and elongating the primer using an enzyme that has reverse transcriptase activity (e.g., a reverse transcriptase, a polymerase that has reverse transcriptase activity, and/or an enzyme that has been engineered to comprise reverse transcriptase activity). In some embodiments, converting RNAs of the plurality of RNAs into RNA:cDNA hybrids comprises using a reverse transcriptase and a plurality of primers that are complementary to the RNAs of the plurality of RNAs. Suitable reverse transcriptase for use in the methods of the present disclosure include, but are not limited to, a Reverse Transcriptase Xenopolymeras (RTX) enzyme, a Moloney murine leukemia virus (MMLV) reverse transcriptase (or variant thereof), and an avian myeloblastosis virus (AMV) reverse transcriptase (or variant thereof). In some embodiments, the primer is a polyT primer. In some embodiments, the polyT primer comprises 12-40 (e.g., 12-18, 12-20, 12-25, 12-30, 18-20, 18-25, 18-30, 18-40, 20-25, 25-30, 25-40, or 30-40) deoxythymidines (dT). In some embodiments, the primer is a random primer (e.g., a random hexamer). In some embodiments, the primer is a sequence specific primer (e.g., a primer that is complementary to a target mRNA sequence). In some embodiments, the method does not comprise fragmenting the RNA prior to converting the RNA into an RNA:cDNA hybrid. In some embodiments, the method does not comprise a step of fragmenting the RNA prior to converting the RNA into an RNA:cDNA hybrid. In some embodiments, the method does not comprise a step of fragmenting the RNA (e.g., an mRNA) prior to converting the RNA into an RNA:cDNA hybrid, and the method does comprise: hybridizing the RNA (e.g., an mRNA) with a primer (e.g., a polyT primer, a random hexamer, or a sequence-specific primer) and elongating the primer using an enzyme that has reverse transcriptase activity (e.g., a reverse transcriptase).

In some embodiments, a method of preparing RNA for sequencing comprises fragmenting RNA:cDNA hybrids into RNA:cDNA hybrid fragments using a ribonuclease and a single-strand-specific nuclease (e.g., as described herein). In some embodiments, fragmenting the RNA:cDNA hybrids into RNA:cDNA hybrid fragments comprises (a) cleaving the RNA of the RNA:cDNA hybrid using a ribonuclease (e.g., RNaseH) to produce corresponding single strand regions of the cDNA. and (b) cleaving the corresponding single stranded regions of the cDNA using a single-strand-specific nuclease (e.g., nuclease P1 or nuclease S1) to produce RNA:cDNA hybrid fragments. In some embodiments, the ribonuclease (e.g., RNaseH) is present at a concentration of about 0.0005 to about 0.025 ng/μL (e.g., about 0.0015 ng/μL, about 0.0025 ng/μL, about 0.0035 ng/μL, about 0.0045 ng/μL, about 0.0055 ng/μL, about 0.0065 ng/μL, about 0.0075 ng/μL, about 0.0085 ng/μL, about 0.0095 ng/μL, about 0.001 ng/μL, about 0.002 ng/μL, about 0.003 ng/μL, about 0.004 ng/μL, about 0.005 ng/μL, about 0.006 ng/μL, about 0.007 ng/μL, about 0.008 ng/μL, about 0.009 ng/μL, about 0.010 ng/μL, about 0.015 ng/μL, or about 0.020 ng/μL). As used herein, the term "about," as applied to one or more values of interest, refers to a value that is similar to a stated reference value. In some embodiments, the term "about" refers to a range of values that fall within 5%, within 4%, within 3%, within 2, within 1%, or less in either direction (greater than or less than) of the state reference value unless otherwise stated or otherwise evidenced from the context.

In some embodiments, the single-strand-specific nuclease (e.g., nuclease P1 or nuclease S1) is present at a concentration of about 5 to about 30 ng/μL (e.g., about 10 ng/μL, about 15 ng/μL, about 20 ng/μL, or about 25 ng/μL). One of ordinary skill in the art can appreciate that the appropriate concentration of ribonuclease (e.g., RNaseH) and/or single-strand-specific nuclease (e.g., nuclease P1 or nuclease S1) is dependent on the desired average fragmentation length, which is in turn influenced by the choice of sequencing platform. For example, short-read sequencing platforms like ILLUMINA sequencing platforms and ION TORRENT sequencing platforms are typically most efficient at sequencing fragments that are 250-600 bp in length. In some embodiments, a next-generation sequencing platform used in a method described herein is an ILLUMINA, ELEMENT, PACBIO, nanopore, SINGULAR, ULTIMA, MGI sequencing, ION TORRENT, or SOLID next-generation sequencing platform.

In some embodiments, a method of preparing RNA for sequencing comprises converting RNA:cDNA hybrid fragments into double stranded DNA (e.g., second strand synthesis). Converting RNA:cDNA hybrid fragments into double stranded DNA may be performed in any suitable way. In some embodiments, converting RNA:cDNA hybrid fragments into double stranded DNA comprising amplifying the cDNA of RNA:cDNA hybrid fragments using a polymerase (e.g., a polymerase that can use RNA as a primer). In some embodiments, the polymerase is *E. coli* Pol I. In some embodiments, the polymerase is *E. coli* DNA Pol 1, T4 DNA Pol, T7 DNA pol, Bsu DNA Pol, Bst DNA Pol, Full Length, Bst DNA Pol, Large Fragment, Phi29 DNA Pol, Taq, KlenTaq, Klenow Fragment, and DNA Pol 1, or Large (Klenow) Fragment. In some embodiments, converting RNA:cDNA hybrid fragments into double stranded DNA comprising amplifying the cDNA of RNA:cDNA hybrid fragments using a polymerase comprises using one or more of *E. coli* DNA Pol 1, T4 DNA Pol, T7 DNA pol, Bsu DNA Pol, Bst DNA Pol, Full Length, Bst DNA Pol, Large Fragment, Phi29 DNA Pol, Taq. KlenTaq, Klenow Fragment, and DNA Pol 1, and Large (Klenow) Fragment.

In some embodiments, the method comprises combining an RNA:cDNA hybrid, a ribonuclease (e.g., RnaseH), a single-strand-specific nuclease (e.g., nuclease P1 or nuclease S1), and a polymerase (e.g., *E. coli* Pol I) into a single reaction mixture. In some embodiments, the ribonuclease (e.g., RNaseH) is present at a concentration of about 0.0005 to about 0.025 ng/μL (e.g., about 0.005 ng/μL, about 0.0015 ng/μL, about 0.0025 ng/μL, about 0.0035 ng/μL, about 0.0045 ng/μL, about 0.0055 ng/μL, about 0.0065 ng/μL, about 0.0075 ng/μL, about 0.0085 ng/μL, about 0.0095 ng/μL, about 0.001 ng/μL, about 0.002 ng/μL, about 0.003 ng/μL, about 0.004 ng/μL, about 0.005 ng/μL, about 0.006 ng/μL, about 0.007 ng/μL, about 0.008 ng/μL, about 0.009 ng/μL, about 0.010 ng/μL, about 0.015 ng/μL, about 0.020 ng/μL, or about 0.025 ng/μL). In some embodiments, the single-strand-specific nuclease (e.g., nuclease P1 or nuclease S1) is present at a concentration of about 5 to about 30 ng/μL (e.g., about 5 ng/μL, about 10 ng/μL, about 15 ng/μL, about 20 ng/μL, about 25 ng/μL, or about 30 ng/μL). In some embodiments, the ribonuclease (e.g., RNaseH) and the single-strand-specific nuclease (e.g., nuclease P1 or nuclease S1) are present at a ratio between about 0.005:30 to about 0.025:5. In some embodiments, the ribonuclease (e.g., RNaseH) and the single-strand-specific nuclease (e.g., nuclease P1 or nuclease S1) are present at a ratio of about 0.005:5, about 0.005:10, about 0.005:15, about 0.005:20, about 0.005:25, about 0.005:30, about 0.0075:5, about 0.0075:10, about 0.0075:15, about 0.0075:20, about 0.0075:25, about 0.0075:30, about 0.01:5, about 0.01:10, about 0.01:15, about 0.01:20, about 0.01:25, about 0.01:30, about 0.0125:5, about 0.0125:10, about 0.0125:15, about 0.0125:20, about 0.0125:25, about 0.0125:30, about 0.015:5, about 0.015:10 about 0.015:15, about 0.015:20, about 0.015:25, about 0.015:30, about 0.0175:5, about 0.0175:10, about 0.0175:15, about 0.0175:20, about 0.0175:25, about 0.0175:30, about 0.02:5, about 0.02:10, about 0.02:15, about 0.02:20, about 0.02:25, about 0.02:30, about 0.025:5, about 0.025:10, about 0.025:15, about 0.025:20, about 0.025:25, or about 0.025:30. In some embodiments, the polymerase (e.g., *E. coli* Pol I) is present at a concentration of about 5 ng/μL to about 50 ng/μL (e.g., about 5 ng/μL, about 10 ng/μL, about 15 ng/μL, about 20 ng/μL, about ng/μL, about 30 ng/μL, about 35 ng/μL, about 40 ng/μL, about 45 ng/μL, or about 50 ng/μL).

In some embodiments, the method comprises first combining RNA:cDNA hybrid, the ribonuclease, the single-strand-specific nuclease, and zinc ion and incubating the single reaction mixture; then, after incubation, combining a polymerase, magnesium ion, and a zinc ion chelator (e.g., EDTA or EGTA) into the single reaction mixture. In some embodiments, the zinc ion is present at a concentration of about 0.00032 mM to about 5 mM (e.g., about 0.0032 mM, about 0.0002 mM, about 0.0001 mM, about 0.005 mM, about 0.001 mM, about 0.05 mM, about 0.01 mM, about 0.5 mM, about 0.1 mM, about 1 mM, about 2 mM, about 3 mM, about 4 mM, or about 5 mM). In some embodiments, the magnesium ion is present at a concentration of about 1 to about 10 mM (e.g., about 1 mM, about 2 mM, about 3 mM, about 4 mM, about 5 mM, about 6 mM, about 7 mM, about 8 mM, about 9 mM, or about 10 mM). In some embodiments, the zinc ion chelator is present at a concentration of about 0.01 mM to about 7 mM (e.g., about 0.001 mM, about 0.075 mM, about 0.05 mM, about 0.025 mM, about 0.01 mM, about 0.75 mM, about 0.5 mM, about 0.25 mM, about 0.1 mM, about 1 mM, about 2 mM, about 3 mM, about 4 mM, about 5 mM, about 6 mM, or about 7 mM).

In some embodiments, the method further comprises A-tailing a double stranded DNA (e.g., using any suitable method). For example, in some embodiments, A-tailing a double-stranded DNA comprises combining double-stranded DNA with a high-fidelity polymerase. In some embodiments, A-tailing a double stranded DNA produces a dsDNA comprising an adenine nucleotide (A) at the 3' end of the dsDNA. In some embodiments, A-tailing a double-stranded DNA produces a sticky-end DNA comprising a 3'-A overhang.

In some embodiments, a method further comprises ligating sequencing adapters (e.g., ILLUMINA sequencing adapters) to a double stranded DNA (e.g., an A-tailed double stranded DNA). A "sequencing adapter" refers to a polynucleotide that is added (e.g., ligated) to an end (e.g., 3' and/or 5') of a target polynucleotide (e.g., an A-tailed double stranded DNA) for use in sequencing of the target polynucleotide. In some embodiments, the sequencing adapter may be used for sequencing using a particular sequencing platform (e.g., ILLUMINA, PACBIO, nanopore, ELEMENT, SINGULAR, ION TORRENT, ULTIMA, or MGI sequencing). For example, ILLUMINA p5 and p7 adapters may be used for sequencing on an ILLUMINA sequencing platform. ILLUMINA sequencing adapters are well known in the art and can be found, for example, on the worldwide web at support-docs.illumina.com/SHARE/AdapterSequences/Content/SHARE/FrontPages/AdapterSeq.htm (Accessed Sep. 23, 2025), incorporated herein by reference.

In some embodiments, methods of the present disclosure reduce the time required to prepare RNA for next-generation sequencing compared to current methods (see FIGS. 1A-1B). Additionally, methods of the present disclosure, in some embodiments, does not require use of a DNA library preparation kit (e.g. a double stranded DNA fragmentation step).

In some embodiments, this disclosure provides a method comprising combining a RNA:DNA hybrid, a ribonuclease, and a single-strand-specific nuclease. In some embodiments, the ribonuclease (e.g., RNaseH) is present at a concentration of about 0.0005 to about 0.025 ng/μL (e.g., about 0.0015 ng/μL, about 0.0025 ng/μL, about 0.0035 ng/μL, about 0.0045 ng/μL, about 0.0055 ng/μL, about 0.0065 ng/μL, about 0.0075 ng/μL, about 0.0085 ng/μL, about 0.0095 ng/μL, about 0.001 ng/μL, about 0.002 ng/μL, about 0.003 ng/μL, about 0.004 ng/μL, about 0.005 ng/μL, about 0.006 ng/μL, about 0.007 ng/μL, about 0.008 ng/μL, about 0.009 ng/μL, about 0.010 ng/μL, about 0.015 ng/μL, or about 0.020 ng/μL). In some embodiments, the single-strand-specific nuclease (e.g., nuclease P1 or nuclease S1) is present at a concentration of 0.5-100 ng/μL. 1-100 ng/μL. 5-100 ng/μL. 0.5-75 ng/μL. 0.5-50 ng/μL. 0.5-25 ng/μL, 3-100 ng/μL.

3-75 ng/μL. 3-50 ng/μL. 3-25 ng/μL, 10-100 ng/μL, 10-75 ng/μL, 10-50 ng/μL, 10-25 ng/μL, 25-100 ng/μL. 25-75 ng/μL. 25-50 or ng/μL, 40-100 ng/μL, 40-75 ng/μL, 40-50 or ng/μL. In some embodiments, the single-strand-specific nuclease (e.g., nuclease P1 or nuclease S1) is present at a concentration of about 25 to about 75 ng/μL (e.g., about 30 ng/μL, about 40 ng/μL, about 50 ng/μL, about 60 ng/μL, about 70 ng/μL, or about 65 ng/μL). In some embodiments, the single-strand-specific nuclease (e.g., nuclease P1 or nuclease S1) is present at a concentration of about 5 to about 30 ng/μL (e.g., about 10 ng/μL, about 15 ng/μL, about 20 ng/μL, or about 25 ng/μL). In some embodiments, the ribonuclease (e.g., RNaseH) and the single-strand-specific nuclease (e.g., nuclease P1 or nuclease S1) are present at a ratio between about 0.005:5, about 0.005:10, about 0.005:15, about 0.005:20, about 0.005:25, about 0.005:30, about 0.0075:5, about 0.0075:10, about 0.0075:15, about 0.0075:20, about 0.0075:25, about 0.0075:30, about 0.01:5, about 0.01:10, about 0.01:15, about 0.01:20, about 0.01:25, about 0.01:30, about 0.0125:5, about 0.0125:10, about 0.0125:15, about 0.0125:20, about 0.0125:25, about 0.0125:30, about 0.015:5, about 0.015:10 about 0.015:15, about 0.015:20, about 0.015:25, about 0.015:30, about 0.0175:5, about 0.0175:10, about 0.0175:15, about 0.0175:20, about 0.0175:25, about 0.0175:30, about 0.02:5, about 0.02:10, about 0.02:15, about 0.02:20, about 0.02:25, about 0.02:30, about 0.025:5, about 0.025:10, about 0.025:15, about 0.025:20, about 0.025:25, or about 0.025:30. In some embodiments, the combining occurs between 22-62° C. (e.g., 22-62° C., 32-62° C., 32-52° C., 37-47° C., or 40-44° C.). In some embodiments, the combining occurs for less than one hour (e.g., less than 30 minutes, less than 10 minutes, or less than 5 minutes). In some embodiments, the combining occurs for between 5-30 minutes (e.g., between 5-20 minutes, between 5-15 minutes, between 5-10 minutes, between 10-20 minutes, between 10-15 minutes, or between 15-20 minutes).

In some embodiments, the method comprises combining an RNA:DNA hybrid, a ribonuclease, and a single-strand-specific nuclease in a reaction mixture having a pH of 7-9.7-8.8-9, or 7.5-8.5. In some embodiments the reaction mixture has a pH of about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9 or about 9. In some embodiments, a buffer of the reaction mixture comprises Tris, HEPES, acetate, or phosphate (e.g., phosphate buffered Saline (PBS)). In some embodiments, the buffer comprises one or more of a Tris buffer, a HEPES buffer, an acetate buffer, or phosphate buffered Saline (PBS) buffer. In some embodiments, a buffer comprising Tris comprises Tris-HCl, Tris-glycine, TRIS-EDTA, Tris-Acetate, Tris-KCL, Tris-KBR, Tris-NaCl, Tris-Citrate, or Tris-Borate. In some embodiments, a buffer comprising acetate comprises acetic acid-sodium acetate, Acetic acid-potassium acetate, or Tris-acetate. In some embodiments, a buffer comprising HEPES comprises a HEPES-NaOH buffer, a HEPES-KOH buffer, or a HEPES-MES buffer. In some embodiments, a buffer comprising PBS comprises NaCl, KCl, $Na_2HPO_4$ and/or $KH_2PO_4$. In some embodiments, the reaction mixture comprises buffers having a molarity of 10-150 mM, 10-125 mM, 10-100 mM, 10-75 mM, 10-50 mM, 10-25 mM, 25-150 mM, 25-125 mM, 25-100 mM, 25-75 mM, 25-50 mM, 50-150 mM, 50-125 mM, 50-100 mM, or 50-75 mM. In some embodiments, the reaction mixture comprises buffers having a molarity of about 10 mM, about 25 mM, about 50 mM, about 75 mM, about 100 mM, about 125 mM or about 150 mM.

Reaction Mixtures

In some embodiments, this disclosure provides a reaction mixture comprising an RNA:DNA hybrid, a ribonuclease, and a single-strand-specific nuclease. In some embodiments, the ribonuclease of the reaction mixture is a RNase. In some embodiments, the RNase is *E. coli* RNase H, Tth RNaseH (Thermostable RNase H), RNase If, or RNase A. In some embodiments, the ribonuclease (e.g., RNaseH) is present at a concentration of about 0.0005 to about 0.025 ng/μL (e.g., about 0.005 ng/μL, about 0.0015 ng/μL, about 0.0025 ng/μL, about 0.0035 ng/μL, about 0.0045 ng/μL, about 0.0055 ng/μL, about 0.0065 ng/μL, about 0.0075 ng/μL, about 0.0085 ng/μL, about 0.0095 ng/μL, about 0.001 ng/μL, about 0.002 ng/μL, about 0.003 ng/μL, about 0.004 ng/μL, about 0.005 ng/μL, about 0.006 ng/μL, about 0.007 ng/μL, about 0.008 ng/μL, about 0.009 ng/μL, about 0.010 ng/μL, about 0.015 ng/μL, about 0.020 ng/μL, or about 0.025 ng/μL). In some embodiments, the single-strand-specific nuclease of the reaction mixture is nuclease P1, nuclease S1, Red, ExoVII, Mung Bean Nuclease or Micrococcal Nuclease. In some embodiments, the single-strand-specific nuclease of the reaction mixture is nuclease P1. In some embodiments, the single-strand-specific nuclease of the reaction mixture is nuclease S1. In some embodiments, the single-strand-specific nuclease (e.g., nuclease P1 or nuclease S1) is present at a concentration of 0.5-100 ng/μL. 1-100 ng/μL. 5-100 ng/μL, 0.5-75 ng/μL, 0.5-50 ng/μL, 0.5-25 ng/μL, 3-100 ng/μL, 3-75 ng/μL, 3-50 ng/μL. 3-25 ng/μL, 10-100 ng/μL, 10-75 ng/μL, 10-50 ng/μL, 10-25 ng/μL, 25-100 ng/μL, 25-75 ng/μL, 25-50 or ng/μL, 40-100 ng/μL, 40-75 ng/μL, 40-50 or ng/μL. In some embodiments, the single-strand-specific nuclease (e.g., nuclease P1 or nuclease S1) is present at a concentration of about 25 to about 75 ng/μL (e.g., about 30 ng/μL, about 40 ng/μL, about 50 ng/μL, about 60 ng/μL, about 70 ng/μL, or about 65 ng/μL). In some embodiments, the single-strand-specific nuclease (e.g., nuclease P1 or nuclease S1) is present at a concentration of about 5 to about 30 ng/μL (e.g., about 5 ng/μL, about 10 ng/μL, about 15 ng/μL, about 20 ng/μL, about 25 ng/μL, or about 30 ng/μL). In some embodiments, the ribonuclease (e.g., RNaseH) and the single-strand-specific nuclease (e.g., nuclease P1 or nuclease S1) are present at a ratio between about 0.005:30 to about 0.025:5. In some embodiments, the ribonuclease (e.g., RNaseH) and the single-strand-specific nuclease (e.g., nuclease P1 or nuclease S1) are present at a ratio of about 0.005:5, about 0.005:10, about 0.005:15, about 0.005:20, about 0.005:25, about 0.005:30, about 0.0075:5, about 0.0075:10, about 0.0075:15, about 0.0075:20, about 0.0075:25, about 0.0075:30, about 0.01:5, about 0.01:10, about 0.01:15, about 0.01:20, about 0.01:25, about 0.01:30, about 0.0125:5, about 0.0125:10, about 0.0125:15, about 0.0125:20, about 0.0125:25, about 0.0125:30, about 0.015:5, about 0.015:10 about 0.015:15, about 0.015:20, about 0.015:25, about 0.015:30, about 0.0175:5, about 0.0175:10, about 0.0175:15, about 0.0175:20, about 0.0175:25, about 0.0175:30, about 0.02:5, about 0.02:10, about 0.02:15, about 0.02:20, about 0.02:25, about 0.02:30, about 0.025:5, about 0.025:10, about 0.025:15, about 0.025:20, about 0.025:25, or about 0.025:30.

In some embodiments, the reaction mixture further comprises zinc ion. In some embodiments, the zinc ion is present at a concentration of about 0.00032 mM to about 5 mM (e.g., about 0.0032 mM, about 0.0002 mM, about 0.0001 mM, about 0.005 mM, about 0.001 mM, about 0.05 mM, about 0.01 mM, about 0.5 mM, about 0.1 mM, about 1 mM, about 2 mM, about 3 mM, about 4 mM, or about 5 mM). In some embodiments, the reaction mixture further comprises magnesium ion. In some embodiments, the magnesium ion is present at a concentration of about 0.1 to about 10 mM (e.g., about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, about 5 mM, about 6 mM, about 7 mM, about 8 mM, about 9 mM, or about 10 mM). In some embodiments, the reaction mixture further comprises potassium ion. In some embodiments, the magnesium ion is present at a concentration of about 0.1 to about 1 mM magnesium ion. In some embodiments, the magnesium ion is present at a concentration of about 1 to about 10 mM magnesium ion.

In some embodiments, the reaction mixture further comprises a polymerase (e.g., *E. coli* Pol I). In some embodiments, the polymerase (e.g., *E. coli* Pol I) is present at a concentration of about 5 ng/μL to about 50 ng/μL (e.g., about 5 ng/μL, about 10 ng/μL, about 15 ng/μL, about 20 ng/μL, about 25 ng/μL, about 30 ng/μL, about 35 ng/μL, about 40 ng/μL, about 45 ng/μL, or about 50 ng/μL).

In some embodiments, the reaction mixture comprises RNA:DNA hybrid, a ribonuclease (e.g., RNaseH), a single-strand-specific nuclease (e.g., nuclease P1), a polymerase (e.g., *E. coli* Pol I), zinc ion, and magnesium ion. In some embodiments, the reaction mixture comprises RNA:DNA hybrid, a ribonuclease (e.g., RNaseH), a single-strand-specific nuclease (e.g., nuclease S1), a polymerase (e.g., *E. coli* Pol I), zinc ion, and magnesium ion.

Kits

In some embodiments, this disclosure provides kits comprising a ribonuclease; and a single-strand-specific nuclease. In some embodiments, the ribonuclease of the kit is a RNase. In some embodiments, the RNase is RNase is *E. coli* RNase H, Tth RNaseH (Thermostable RNase H), RNase If, or RNase A. In some embodiments, the single-strand-specific nuclease of the kit is nuclease P1, nuclease S1, Red, ExoVII, Mung Bean Nuclease or Micrococcal Nuclease. In some embodiments, the single-strand-specific nuclease of the kit is nuclease P1. In some embodiments, the single-strand-specific nuclease of the kit is nuclease S1. In some embodiments, the kit further comprises zinc ion. In some embodiments, the kit further comprises reagents for first strand synthesis. In some embodiments, reagents for first strand synthesis comprise a primer (e.g., a target specific primer, a polyT primer, or a random hexamer) and an enzyme that has reverse transcriptase activity (e.g., a reverse transcriptase). In some embodiments, the kit further comprises reagents for second strand synthesis. In some embodiments, the reagents for second strand synthesis include a polymerase. In some embodiments, the kit includes one or more of *E. coli* DNA Pol 1, T4 DNA Pol, T7 DNA pol, Bsu DNA Pol, Bst DNA Pol, Full Length, Bst DNA Pol, Large Fragment, Phi29 DNA Pol, Taq. KlenTaq, Klenow Fragment, and DNA Pol 1, or Large (Klenow) Fragment. In some embodiments, the reagents for second strand synthesis comprise a polymerase (e.g., *E. coli* Pol I) and a zinc ion chelator (e.g., EDTA or EGTA). In some embodiments, the kit comprises primers (e.g., polyT primers), a reverse transcriptase, a ribonuclease (e.g., RNaseH), a single-strand-specific nuclease (e.g., nuclease P1), zinc ion, a polymerase (e.g., *E. coli* Pol I), magnesium ion, and a zinc ion chelator (e.g., EDTA or EGTA). In some embodiments, the kit further comprises reagents for poly-A tailing. In some embodiments, the kit further comprises sequencing adapters and reagents for ligating the sequencing adapters to double stranded DNA.

In some embodiments, the method of fragmenting an RNA:DNA hybrid, comprises: (i) cleaving the DNA of the RNA:DNA hybrid using a nuclease to produce single strand regions of the RNA; and (ii) cleaving the single stranded regions of the RNA using a single-strand-specific nuclease to produce RNA:DNA hybrid fragments.

EXAMPLES

Example 1. Method for Fragmenting RNA:DNA Hybrids

RNA sequencing (RNA-seq) has become an indispensable tool in molecular biology. Coupled with advances in massively parallel next generation sequencing (NGS), RNA-seq affords high-throughput transcriptome profiling, facilitating differential gene expression analysis, single nucleotide polymorphism identification and transcript isoform detection.

A typical RNA-seq workflow first requires RNA extraction, followed by either mRNA enrichment (e.g., via poly(A) selection) or ribosomal RNA depletion, cDNA synthesis ($1^{st}$ and $2^{nd}$ strand synthesis (SS)), adapter ligation, and sequencing. An important step of preparing a high-quality library for NGS is the generation of fragments that have a size distribution centered around an ideal average length. For example, the ideal average length for Illumina sequencing platforms is normally a few hundred base pairs. Fragmentation and correctly sized inserts are commonly achieved through two methods:

1. The original method relies on converting the RNA to full-length double-stranded cDNA by cDNA synthesis ($1^{st}$ strand synthesis to obtain a RNA:DNA hybrid, typically using an oligo dT), followed by $2^{nd}$ strand synthesis to obtain full-length double-stranded cDNA, then fragmentation either enzymatically or mechanically (FIG. 1B). This method often uses pre-enriched RNA. Once double-stranded cDNA is prepared, the sample can be treated like a DNA library.
2. The interaction of heat, pH and $Mg^{2+}$ concentration to fragment the RNA directly before cDNA synthesis (FIG. 1A). The combination of heat (e.g., 55° C.-95° C.) and a metal ion (e.g., $Mg^{2+}$, $Mn^{2+}$, $Zn^{2+}$) randomly fragments the RNA into smaller pieces. This workflow employs a randomer (e.g., a hexamer) priming method to convert fragmented RNA to double-stranded cDNA (dscDNA) via $1^{st}$ then $2^{nd}$ strand synthesis, then A-tailing and ligation. Due to the randomer priming method, unwanted RNA species (e.g., rRNA) need to be removed prior to cDNA synthesis. This approach is the current standard and is used in many commercially-available library preparation kits.

An alternative approach involves the fragmentation of the product of the $1^{st}$ strand synthesis reaction (i.e., an RNA: DNA hybrid), followed by normal $2^{nd}$ strand synthesis to yield size-appropriate double-stranded cDNA fragments ready for adapter ligation and sequencing (FIG. 1C). Such an approach would require a unique combination of endonucleases that can collectively cleave both the RNA and DNA complements of an RNA:DNA hybrid to yield blunt-end fragments. This Example describes a method for fragmenting RNA:DNA hybrids, which facilitates rapid stranded library preparation for RNA-seq and significantly reduces workflow time.

Fragmentation of RNA:DNA hybrids requires a mixture of endonucleases that can collectively cleave both the RNA and DNA components. The methods presented in this Example make use of a non-sequence-specific ribonuclease (e.g., RNase H) in combination with a single-strand-specific nuclease (nuclease P1). The non-sequence-specific ribonuclease (e.g., RNase H) component catalyzes the nicking of RNA in RNA:DNA hybrid molecules, resulting in single-stranded regions on the complementary DNA strand which are then susceptible to cleavage by the single-strand specific nuclease (e.g., Nuclease P1). The resulting reaction yields blunt-end or near blunt-end RNA:DNA hybrid fragments, the size of which can be tuned using different concentrations of non-sequence-specific ribonuclease (e.g., RNase H) and single-strand specific nuclease (e.g., Nuclease P1), or temperature and time. The fragmented RNA:DNA hybrids can then undergo $2^{nd}$ strand synthesis to form double-stranded DNA fragments ready for adapter ligation and high-throughput sequencing.

Figure 3:
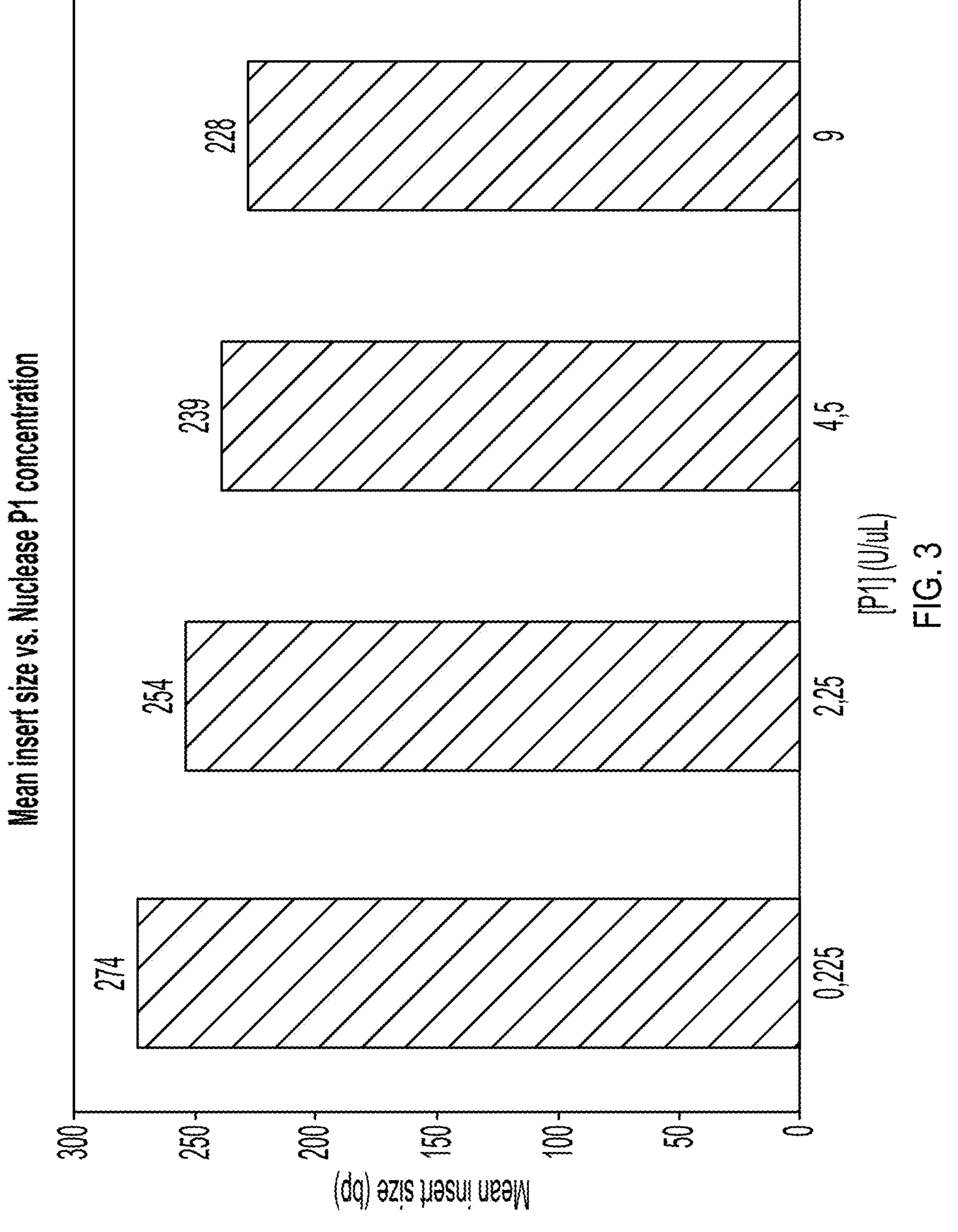
FIG. 3 shows mean insert size response to nuclease P1 concentration.

Both a non-sequence-specific ribonuclease (e.g., RNase H) and a single-strand-specific nuclease (e.g., Nuclease P1) are important for fragmentation of RNA:DNA hybrids. This is evident by the effect of single-strand-specific nuclease concentration on fragment size. While keeping RNase H concentration constant, adding more Nuclease P1 to the $1^{st}$ strand synthesis product resulted in more fragmentation, evidenced by smaller mean fragment sizes (FIG. 3). Thus, there is a direct relationship between the amount of single-strand-specific nuclease present and the resulting degree of RNA:DNA fragmentation.

Figure 4:
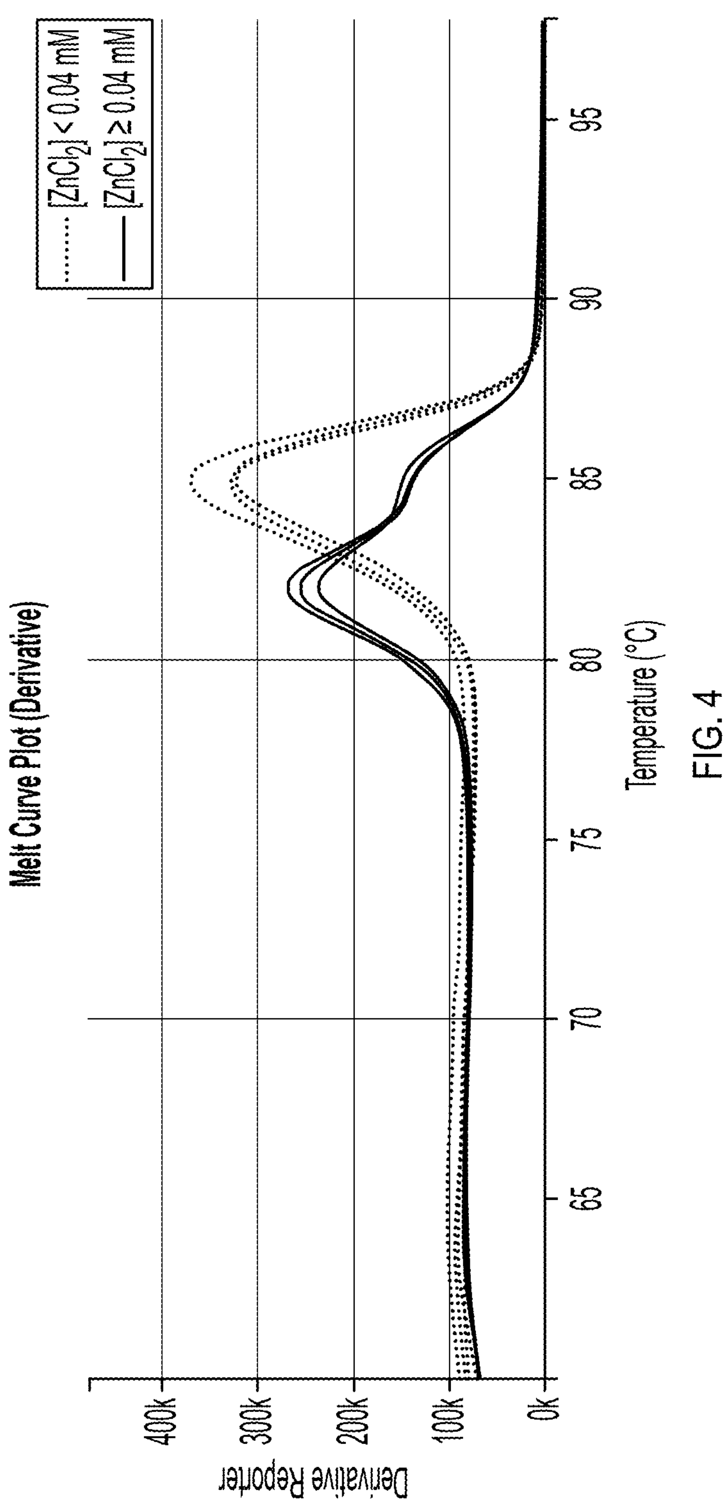
FIG. 4 shows qPCR melt curve analysis of library formation with varying ZnCl2 concentrations.

Furthermore, when a combination of non-sequence-specific ribonuclease (e.g., *E. coli* RNase H) and single-strand-specific nuclease (e.g., Nuclease P1, a zinc-dependent single-strand-specific nuclease) are added to the $1^{st}$ strand synthesis product (i.e., full-length RNA:DNA hybrid), fragmentation only occurs when sufficient essential cofactors (e.g., $Zn^{2+}$, $Mg^{2+}$) are present. This is evidenced by qPCR melt curve analysis of library formation under varying ZnCl2 concentrations (FIG. 4). DNA libraries exhibit melt curves with a peak around 82° C., while adapter dimers (i.e., no library) peak around 85° C. Thus, using library yield as a proxy for successful fragmentation of the RNA:DNA hybrids, fragmentation was observed when the ZnCl2 concentration was at least 0.04 mM since Nuclease P1 requires $Zn^{2+}$ for catalysis. That is, when Nuclease P1 is not active due to the absence of an essential cofactor ($Zn^{2+}$), fragmentation does not occur.

Thus, it is the unique combination of a ribonuclease (e.g., RNase H) and a single-strand-specific nuclease that facilitates the fragmentation of RNA:DNA hybrids. To further demonstrate this, 100 ng total RNA (Universal Human Reference RNA, Agilent, Cat #740000) was used as input for the generation of libraries in preparation for RNA-seq. After the generation of RNA-DNA hybrid molecules following $1^{st}$ strand cDNA synthesis, the samples were treated to one of the following conditions:

| Condition | *E. coli* RNase H | Single-strand-specific nuclease (P1 or S1) |
|---|---|---|
| Control | No | No |
| Condition 1 | Yes | No |
| Condition 2 | No | Yes |
| Condition 3 | Yes | Yes |

Following the RNA:DNA fragmentation step, all samples underwent $2^{nd}$ strand cDNA synthesis. The double-stranded cDNA molecules were then subjected to adapter ligation and quality screening by qPCR and TapeStation analysis, followed by RNA-seq and downstream analyses.

Figure 5:
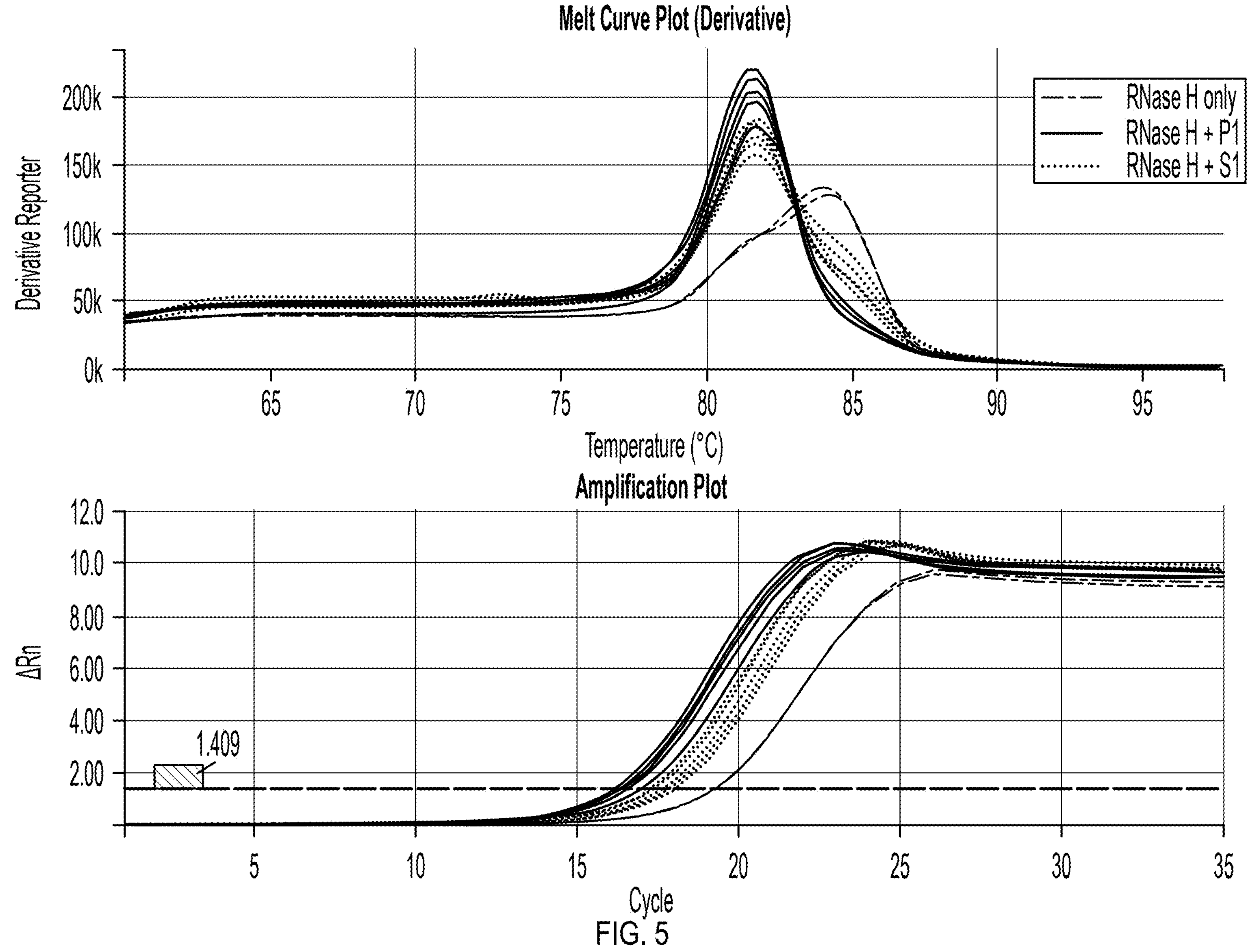
FIG. 5 shows qPCR analysis of library formation in the absence (RNase H only) or presence of single-strand-specific nucleases (RNase H+P1; RNase H+S1).
Figure 6:
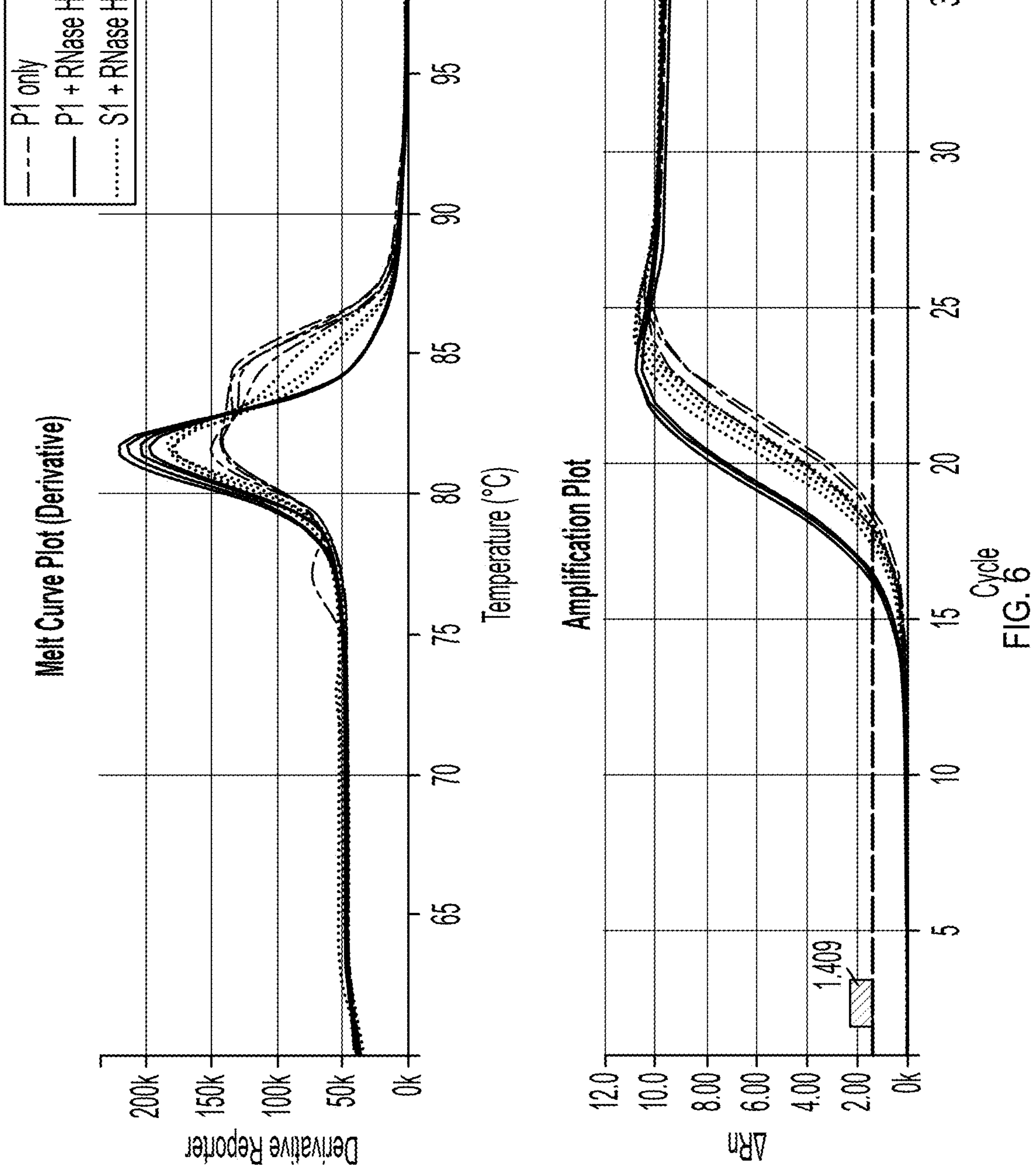
FIG. 6 shows qPCR analysis of library formation in the absence (P1 only) or presence of ribonucleases (P1+RNase H; S1+RNase H).

The post-amplification qPCR quantification plots clearly show that libraries are only formed when both a ribonuclease (e.g., RNase H) and a single-strand-specific nuclease (e.g., P1 or S1) are present. That is, when a ribonuclease (e.g., RNase H) is present but a single-strand-specific nuclease (e.g., P1 or S1) is absent, no library is formed (FIG. 5). Similarly, when a single-strand-specific nuclease (e.g., P1 or S1) is present but a ribonuclease (e.g., RNase) is absent, no library is formed (FIG. 6).

Figure 7:
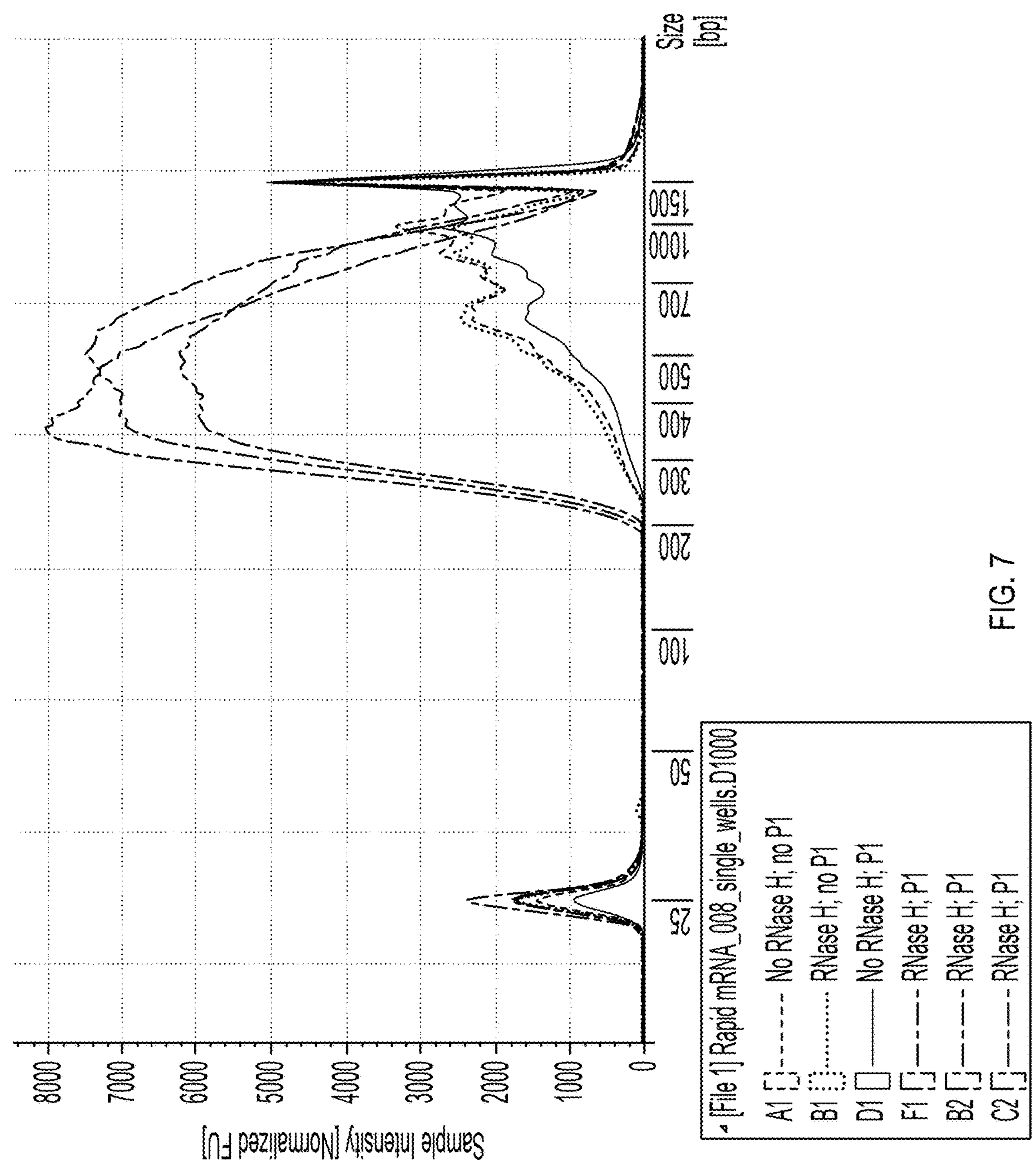
FIG. 7 shows post-amplification TapeStation analysis of samples that underwent library preparation in the absence of ribonuclease RNase H and single-strand-specific nuclease P1 (No RNase H; no P1), in the presence of RNase H and absence of P1 (RNase H; no P1), in the absence of RNase H and presence of P1 (No RNase H; P1), or in the presence of both RNase H and P1 (RNase H; P1, run in triplicate).
Figure 8:
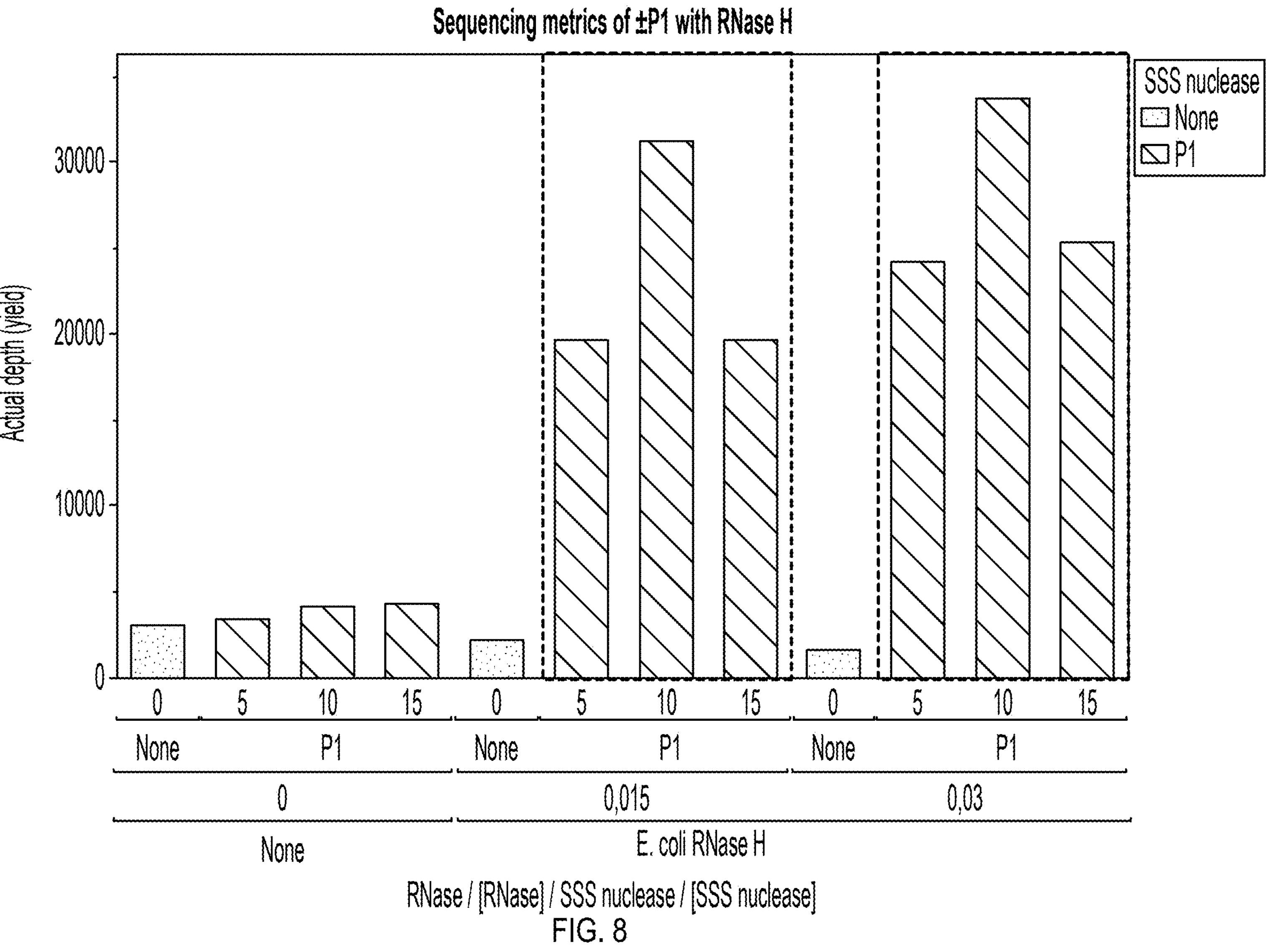
FIG. 8 is a plot of sequencing metrics in the presence of 0 U/μl, 5 U/μl, 10 U/μl, or 15 U/μl single-strand-specific nuclease P1 and 0 U/μl. 0.015 U/μl, or 0.03 U/μl ribonuclease RNase H. Samples that contained both *E. coli* RNase H and P1 are shown boxed.

These results were corroborated by TapeStation analysis of amplified libraries. All samples were amplified for the same number of cycles and analyzed on a TapeStation D1000, highlighting the effects of the absence or presence of ribonuclease (e.g., RNase H) and/or single-strand-specific nuclease (e.g., P1 or S1) (FIG. 7). Typical Illumina libraries (200-500 bp) were only observed conditions where both a ribonuclease and a single-strand-specific nuclease were present (Condition 3), while conditions lacking one or both of the ribonuclease and single-strand-specific nuclease (Control, Condition 1, Condition 2) all showed no library peaks. This trend was also evident in the final sequencing metrics, with the actual depth (a direct indicator of yield in samples that are pooled equi-volume) showing that only samples containing both a ribonuclease and single-strand-specific nuclease (Condition 3) resulted in sequenceable libraries as a result of RNA:DNA hybrid fragmentation (FIG. 8).

This Example describes a method for fragmenting RNA:DNA hybrids and demonstrates that appropriately sized libraries can be formed if the RNA:DNA hybrids following $1^{st}$ strand cDNA synthesis can be fragmented prior to $2^{nd}$ strand cDNA synthesis, for example by using a combination of a ribonuclease (e.g., RNase H) and single-strand-specific nuclease (e.g., Nuclease P1 or S1) that facilitates the desired fragmentation.

Example 2. Evaluating the Effect of Individual Fragmentation Enzymes

To demonstrate the effect of individual fragmentation enzymes, 100 ng total RNA (Universal Human Reference RNA, Agilent Cat #74000) was used as input for library preparation. After $1^{st}$ strand cDNA synthesis, the RNA:DNA hybrid molecules were subjected to fragmentation using 5-30 ng/μL P1 and 0.0005-0.025 ng/μL RNase H. This was followed by $2^{nd}$ strand cDNA synthesis, adapter ligation, sequencing, and downstream analysis. The downstream analysis included characterization of the following metrics:

Sample depth: Measure of yield (read depth on sequencer)

Insert size: Length of DNA sequence between adapters

PCT mRNA: Fraction of bases mapped to regions corresponding to UTRs and coding regions of mRNA transcripts PCT rRNA: Fraction of bases mapped to regions encoding ribosomal RNA PCT PF reads aligned: Fraction of bases that are aligned and pass filter PCT correct strand reads: Fraction of reads corresponding to mRNA transcripts which map to the correct strand of a reference genome Unique genes: Count of unique genes identified (>5 reads per gene)

Figure 9:
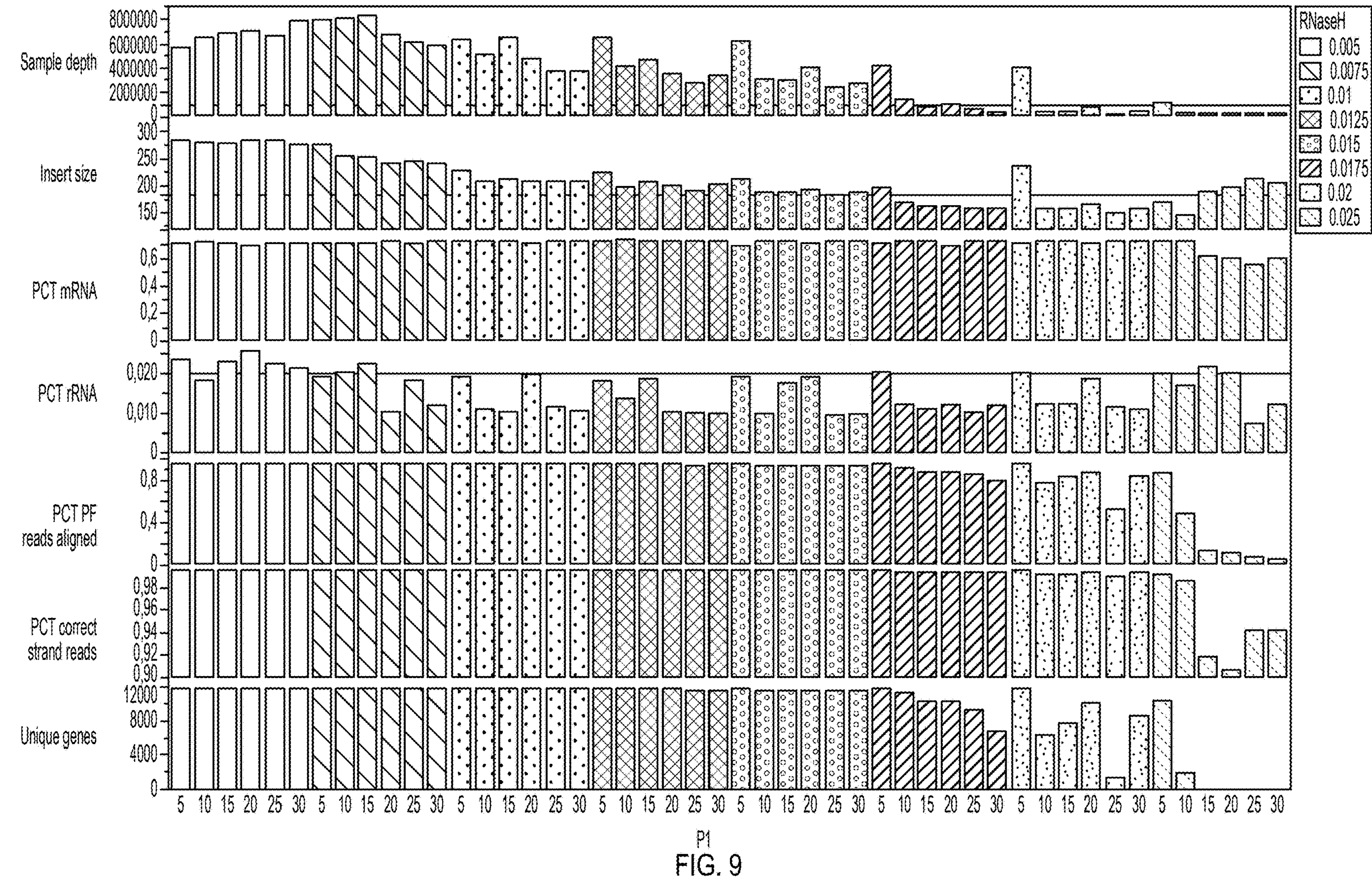
FIG. 9 is a plot of sequencing metrics in the presence of 5 ng/μL, 10 ng/μL. 15 ng/μL, 20 ng/μL, 25 ng/μL, or 30 ng/μL single-strand-specific nuclease P1 and 0.0005 ng/μL, 0.0075 ng/μL, 0.01 ng/μL, 0.0125 ng/μL, 0.015 ng/μL. 0.0175 ng/μL. 0.02 ng/μL, or 0.025 ng/μL ribonuclease RNase H.

Typical libraries with high quality sequencing metrics were observed across a range of P1 and RNase H concentrations, with insert size shifts along both enzyme gradients demonstrating the potential for tunability (FIG. 9).

The invention claimed is:

1. A method of fragmenting an RNA:DNA hybrid, the method comprising:

(i) cleaving the RNA of a RNA:DNA hybrid using a ribonuclease to produce single strand regions of the DNA; and (ii) cleaving the single stranded regions of the DNA using a single-strand-specific nuclease to produce RNA:DNA hybrid fragments.

2. The method of claim 1, wherein the ribonuclease is a non-sequence-specific ribonuclease.

3. The method of claim 2, wherein the non-sequence-specific ribonuclease is an RNase.

4. The method of claim 3, wherein the RNase is RNaseH.

5. The method of claim 1, wherein the single-strand specific nuclease is nuclease P1 or nuclease S1.

6. A method of preparing RNA for sequencing, the method comprising:

(i) converting the RNA into an RNA:cDNA hybrid;

(ii) fragmenting the RNA:cDNA hybrid into RNA:cDNA hybrid fragments using a ribonuclease and a single-strand-specific nuclease; and (iii) converting the RNA:cDNA hybrid fragments into double stranded DNA.

7. The method of claim 6, wherein the RNA:cDNA hybrid fragments are 200-300 base pairs in length.

8. The method of claim 6, wherein the RNA:cDNA hybrid fragments are 100-1500 base pairs in length.

9. The method of claim 6, wherein fragmenting comprises:

(a) cleaving the RNA of the RNA:cDNA hybrid using the ribonuclease to produce single-strand regions of the cDNA; and (b) cleaving the single-stranded regions of the cDNA using the single-strand-specific nuclease to produce RNA:cDNA hybrid fragments.

10. The method of claim 6, wherein (i) converting the RNA into an RNA:cDNA hybrid comprises converting using a reverse transcriptase and primers.

11. The method of claim 10, wherein the primers are poly-T primers, random primers, or target specific primers.

12. The method of claim 6, wherein converting the RNA:cDNA hybrid fragments into double stranded DNA comprises using a polymerase.

13. The method of claim 12, wherein the polymerase is an *E. coli* Pol I.

14. The method of claim 6, comprising combining the RNA:cDNA hybrid, the ribonuclease, the single-strand-specific nuclease, and a polymerase into a single reaction mixture.

15. The method of claim 6, wherein (ii) and (iii) occur contemporaneously.

16. The method of claim 6, further comprising A-tailing the double stranded DNA.

17. The method of claim 6, further comprising ligating sequencing adaptors onto the double stranded DNA.

18. A method of preparing RNA for sequencing, the method comprising:

(i) obtaining a plurality of RNAs;

(ii) converting RNAs of the plurality of RNAs into RNA:cDNA hybrids using a reverse transcriptase and a plurality of primers that are complementary to the RNAs of the plurality of RNAs;

(iii) fragmenting the RNA:cDNA hybrids into RNA:cDNA hybrid fragments, the fragmenting comprising:

(a) cleaving the RNA of the RNA:cDNA hybrid using an RNaseH to produce corresponding single strand regions of the cDNA; and (b) cleaving the corresponding single stranded regions of the cDNA using a nuclease P1 to produce RNA: cDNA hybrid fragments;

(iv) converting the RNA:cDNA hybrid fragments into double stranded DNAs (dsDNAs) using a polymerase;

(v) A-tailing the dsDNAs to produce A tailed dsDNAs; and (vi) attaching sequencing adaptors onto the dsDNAs.

* * * * *